United States Patent [19]

Wuest et al.

[11] Patent Number: 5,001,285

[45] Date of Patent: Mar. 19, 1991

[54] PROCESS FOR THE BROMINATION OF NITRO-ALCOHOLS

[75] Inventors: Willi Wuest, Ratingen; Rainer Eskuchen, Duesseldorf; Herbert Esser, Troisdorf, all of Fed. Rep. of Germany

[73] Assignee: Henkel Kommanditgesellschaft auf Aktien, Duesseldorf-Holthausen, Fed. Rep. of Germany

[21] Appl. No.: 345,516

[22] Filed: May 1, 1989

[30] Foreign Application Priority Data

Apr. 30, 1988 [DE] Fed. Rep. of Germany ....... 3814773

[51] Int. Cl.$^5$ .............................................. C07C 205/14
[52] U.S. Cl. ..................................... 568/924; 568/704
[58] Field of Search ............... 568/924, 927, 707, 933, 568/704, 714, 713

[56] References Cited

U.S. PATENT DOCUMENTS 3,658,921 4/1972 Wessendorf.

FOREIGN PATENT DOCUMENTS 740947 8/1966 Canada.
1768976 7/1968 Fed. Rep. of Germany.

OTHER PUBLICATIONS

*Chemical Abstracts*, vol. 81, Nr. 19, Nov. 11, 1974, p. 475, column 2, No. 119937Y.
*Chemical Abstracts*, vol. 81, Nr. 19, Nov. 11, 1974, p. 553, column 2, No. 59652e.
*Chemical Abstracts*, vol. 80, Nr. 11, Mar. 18, 1974, p. 319, column 1, No. 59447f.
*Patent Abstracts of Japan*, vol. 5, No. 194, Dec. 10, 1981 (C-82) (866).
JO 1132549, Katayama Kagaku Kog, Nov. 17, 1987.

*Primary Examiner*—Robert L. Stoll
*Assistant Examiner*—Valerie Fee
*Attorney, Agent, or Firm*—Ernest G. Szoke; Wayne C. Jaeschke; Henry E. Millson, Jr.

[57] ABSTRACT

A process for the preparation of geminate bromo-nitroalcohols by the bromination of alkali metal or alkaline-earth metal salts of nitroalcohols in aqueous solution, while cooling the reaction mixture so that the maximum reaction temperature does not exceed 30° C. In carrying out the reaction, the aqueous solution of nitroalcohol salt is added to a mixture of bromine and aqueous hydrobromic acid.

13 Claims, No Drawings

PROCESS FOR THE BROMINATION OF NITRO-ALCOHOLS

BACKGROUND OF THE INVENTION

1. Field of the Invention

This invention relates to a process for the bromination of nitro-alcohols on the carbon atom which bears the nitro-group. Nitro-alcohols and bromo-nitro-alcohols are known substances. 2-Bromo-2-nitro-1,3propanediol, for instance, is important as a preservative and a microbicidally active ingredient.

2. Statement of the Related Art

The starting materials generally used for the preparation of bromo-nitro-alcohols, in which the bromo- and nitro-groups are both on the same carbon atom, are nitro-alcohols, which are reacted with elementary bromine.

Thus in Japanese Patent Application 74/70911, cited in Chem. Abstracts, Vol. 81, 119937y (1974), it is proposed to prepare nitro-1,3-propanediol by the reaction of nitromethane and formaldehyde in the presence of aqueous NaOH and to convert this with bromine in dichloroethane to the corresponding bromo compound.

DESCRIPTION OF THE INVENTION

Other than in the operating examples, or where otherwise indicated, all numbers expressing quantities of ingredients or reaction conditions used herein are to be understood as modified in all instances by the term "about".

Against the background of the above prior art, it is an object of the invention to develop a process for carrying out this type of bromination reaction, which takes place without the use of an organic solvent, and to produce the desired bromo-nitro alcohol with a better space-time consumption and a higher yield.

It has surprisingly been found that the bromination reaction can be carried out on an industrial scale at a higher concentration and therefore better space-time consumption if the nitro-alcohol in aqueous solution and in salt-form is added to a solution of bromine/hydrobromic acid. When the sequence of addition is reversed, considerable quantities of by-products are produced.

The present invention therefore relates to a process for the preparation of geminate bromo-nitro-alcohols by the bromination of alkali metal or alkaline-earth metal salts of nitro-alcohols, in which to a mixture of bromine and aqueous hydrobromic acid solution there is added an aqueous solution of an alkali metal or alkaline-earth metal salt of a nitro-alcohol at such a rate that, with external cooling, the maximum reaction temperature does not exceed 30° C.

The external cooling can be carried out by means of a heat exchanger. In this embodiment the mixture of bromine and aqueous hydrobromic acid solution is pumped cyclically over the heat exchanger, and to this mixture before it passes over the heat exchanger is added the aqueous solution of an alkali metal or alkaline-earth metal salt of a nitro-alcohol at a rate such that, with cooling, the temperature does not exceed 30° C.

As the mixture of bromine and hydrobromic acid solution there can be employed mixtures of bromine with a hydrobromic acid solution of 50 to 62% by weight of HBr, and in particular azeotropically distilled aqueous HBr-solution. The proportions (molar) of HBr to bromine in the mixture amount to 1:3 to 1:10, preferably 1:5 to 1:5.5, and more preferably 1:5.3.

According to the invention an alkali metal salt (e.g. the sodium or potassium salt) and/or in so far as it is water soluble, an alkaline-earth metal salt (e.g. the calcium salt) of the nitro-alcohol are then introduced into the above mixture. Alkali metal or alkaline-earth metal salts of many known nitro-alcohols can be reacted. Alkali metal salts of nitro-alcohols are preferred which can be obtained by the reaction of nitro-paraffins having from 1 to 8 C-atoms in the paraffin moiety thereof (and particularly those which can be obtained from nitromethane) with short-chain aldehydes, particularly those with up to 3 carbon atoms, such as formaldehyde, acetaldehyde, propionaldehyde or chloral, with the proviso that they have an acidic hydrogen atom on the C-atom which bears the nitro group.

According to a preferred embodiment of the present process there are used alkali metal and/or alkaline-earth metal salts of 2-nitro-1,3-propanediol. Of these salts the potassium salt is preferred. Aqueous solutions of this potassium salt can for example be used wherein the potassium salt is prepared according to the process set forth in copending application Ser. No. 07/345,517, now pending filed of even date herewith.

In order to be able to carry out the process according to the invention with better space-time consumption, the alkali metal or alkaline-earth metal salts are preferably used in 40 to 60% by weight aqueous solutions or suspensions.

According to the invention the reaction heat, which evolves when the salt is added dropwise to the mixture of bromine and hydrobromic acid solution, is dissipated by external cooling means, e.g. by a heat-exchanger. Plate heat-exchangers or preferably tube bundle heat-exchangers are suitable for this purpose. Heat-exchangers of other constructions can also be used, but it is generally true that as the exchange area falls the rate of addition must also be reduced, because a temperature of 30° C. should not be exceeded in the reaction.

In a preferred procedure for the process the mixture of bromine and hydrobromic acid solution is prepared in an agitator vessel made of corrosion-resistant material, e.g. tantalum, and pumped through a corrosion-resistant tube-reactor by means of a centrifugal pump into the tube bundle heat-exchanger and recycled back into the agitator vessel. The reaction mixture is pumped around until the entire solution of the salt of the nitro-alcohol has been introduced.

According to a preferred embodiment of the invention, if any bromine is present at the end of the reaction, shown by coloration of the solution, this is then reduced by the introduction of a reducing agent, e.g. an aqueous hydroxylamine solution. The hydroxylamine solution can be added gradually dropwise until the reaction mixture is at least substantially decolorized.

The mixture of bromine and 2-bromo-2-nitro-alcohols first obtained in process of the invention can either be processed in a known manner, e.g. by extracting the 2-bromo-2-nitro-alcohol with suitable solvents, or the mixture can be subjected as is to further processing in a subsequent reaction stage.

For example, 2-bromo-2-nitro-1,3-propanediol can be converted directly to 5-bromo-5-nitro-1,3-dioxane without intermediate isolation, as set forth in copending application Ser. No. 07/345,918 filed now abandoned of even date herewith.

2-Bromo-2-nitro-alcohols are important preservatives and microbicides. Moreover, 2-bromo-2-nitro-1,3-propanediol is important as an intermediate for preparing the above-mentioned 5-bromo-5-nitro-1,3-dioxane, which is also used as a microbicidally active agent.

The invention will be illustrated but not limited by the following examples.

EXAMPLES

EXAMPLE 1

Preparation of 2-nitro-1,3-propanediol potassium salt

The procedure was carried out in a pilot plant, consisting of a 0.8 m³ agitator vessel, a centrifugal pump with a throughput rate of 25 m³·h⁻¹; H=40 m and a 12 m² plate heat-exchanger.

229.2 kg of 37% by weight aqueous formaldehyde solution was placed in the agitator vessel, and by pumping the solution over the heat-exchanger and back into the agitator vessel, the solution was cooled to a temperature of 0° to 10° C. Then, over the course of 30 minutes, 201.4 g of a 45% by weight aqueous solution of potassium hydroxide was added, and mixing was effected in the turbulence of the centrifugal pump. The temperature of the mixture was held between 0° and 10° C.

82.1 kg of nitro-methane was added to this mixture over 2 hours. The rate of addition was regulated so that the temperature of the reaction mixture did not exceed 15° C. The temperature was regulated by the rate of inflow of the nitro-methane. The post-reaction time was 15 minutes, and during this time the reaction mixture was pumped cyclically. At the end of the reaction period the residual content of nitro-methane had fallen below 1% by weight. The potassium salt of 2-nitro-1,3-propanediol which was formed, remained in solution at temperatures down to −15° C. 2-Nitro-1,3-propanediol can be produced by neutralizing the salt solution.

EXAMPLE 2

Bromination of 2-nitro-1,3-propanediol potassium salt to 2-bromo-2-nitro-1,3-propanediol Bromination was effected in an enamelled agitator vessel with a volume of 1.3 m³. This was connected via a pipe to a centrifugal pump with a throughput rate of 10 m³/h, H=12 m, and to a 6 qm tube bundle heat-exchanger. The heat-exchanger outlet was connected back to the agitator vessel. 228.3 kg of bromine from a bromine storage container and 35.1 kg of 62% aqueous HBr from another storage container were fed into the agitator vessel and pumped through the product-cooling cycle. Then over the course of 1.5 hours, 512.7 kg of the reaction mixture obtained from Example 1 (i.e. the reaction mixture containing the 2-nitro-1,3-propanediol potassium salt) was added. The reaction temperature was kept below 30° C. throughout the entire reaction period; when the temperature approached 30° C. the rate of inflow of the potassium salt solution was reduced. After the addition was complete and after a post-reaction time of 0.5 hours the excess bromine was reduced in 0.5 hours with 14.8 kg of a 40% by weight of hydroxyl-ammonium chloride solution.

We claim:

1. In a process for the preparation of geminate bromo-nitro-alcohols by the bromation of an alkali metal salt and/or an alkaline-earth metal salt of a nitroalcohol, the improvement wherein an alkali metal salt of a nitroalcohol is added to a mixture of bromine and aqueous hydrobromic acid while controlling the temperature of the reaction mixture so that the temperature of the reaction mixture never exceeds about 30° C., wherein the temperature is controlled by both cooling the reaction mixture and controlling the rate of addition of the salt of the nitroalcohol, and wherein the reaction is carried out in the absence of an organic solvent.

2. The process of claim 1 wherein the aqueous hydrobromic acid has a hydrobromic acid content of from about 50 to about 62% by weight.

3. The process of claim 2 wherein in the mixture of bromine and hydrobromic acid, the molar ratio of hydrobromic acid to bromine is from about 1:3 to about 1:10.

4. The process of claim 3 wherein said molar ratio is from about 1:5 to about 1:5.5.

5. The process of claim 1 wherein the salt of the nitroalcohol is the potassium salt.

6. The process of claim 1 wherein the salt of the nitroalcohol is the potassium salt of 2-nitro-1,3-propanediol.

7. The process of claim 1 wherein the salt of the nitroalcohol is in the form of an aqueous solution containing from about 40 to about 60% by weight of salt.

8. The process of claim 1 wherein the reaction mixture is treated with hydroxylamine until the reaction mixture is substantially colorless.

9. The process of claim 1 wherein the process is carried out with continuous mixing of the reaction mixture.

10. The process of claim 1 wherein the nitroalcohol is a reaction product of a nitro-paraffin having from 1 to 8 carbon atoms in the paraffin moiety and a short-chain aldehyde.

11. The process of claim 10 wherein the short-chain aldehyde contains from 1 to 3 carbon atoms.

12. The process of claim 1 wherein the aqueous hydrobromic acid has a hydrobromic acid content of from about 50 to 62% and the molar ratio of hydrobromic acid to bromine is from about 1:3 to about 1:10; wherein the salt of the nitroalcohol is the potassium salt of 2-nitro-1,3-propanediol; and wherein the process is carried out with continuous mixing of the reaction mixture.

13. The process of claim 12 wherein hydroxylamine is added to the reaction mixture until the reaction mixture is substantially colorless.

* * * * *